United States Patent [19]

Banholzer et al.

[11] Patent Number: 5,770,738

[45] Date of Patent: Jun. 23, 1998

[54] ESTERS OF BI- AND TRICYCLIC AMINO ALCOHOLS, THEIR PREPARATION AND THEIR USE IN PHARMACEUTICAL COMPOSITIONS

[75] Inventors: Rolf Banholzer, Ingelheim am Rhein; Rudolf Bauer, Ockenheim; Richard Reichl, Gau-Algesheim, all of Germany

[73] Assignee: Boehringer Ingelheim KG, Ingelheim am Rhein, Germany

[21] Appl. No.: 412,408

[22] Filed: Mar. 28, 1995

Related U.S. Application Data

[63] Continuation of Ser. No. 117,199, Dec. 2, 1993, abandoned.

[30] Foreign Application Priority Data

Mar. 5, 1992 [WO] WIPO ............... PCT/EP92/00489

[51] Int. Cl.$^6$ ................................... A01N 43/42
[52] U.S. Cl. .................. 514/304; 546/129; 546/130; 546/131
[58] Field of Search .................. 546/125, 126, 546/128, 129, 130, 131; 514/304

[56] References Cited

U.S. PATENT DOCUMENTS

| | | | |
|---|---|---|---|
| 2,782,199 | 2/1957 | Cusic et al. | 546/126 |
| 2,824,106 | 2/1958 | Zeile et al. | 546/131 |
| 2,872,452 | 2/1959 | Zelle et al. | 260/292 |
| 3,145,211 | 8/1964 | Feldkamp et al. | 546/129 |
| 3,502,683 | 3/1970 | Banholzer et al. | 260/292 |
| 3,505,337 | 4/1970 | Zeile et al. | 546/131 |
| 3,583,996 | 6/1971 | Banholzer et al. | 546/112 |
| 3,673,195 | 6/1972 | Yoneda et al. | 260/293.54 |
| 3,808,263 | 4/1974 | Yoneda et al. | 260/293.54 |
| 4,042,700 | 8/1977 | Banholzer et al. | 514/304 |
| 4,411,902 | 10/1983 | Bernareggi et al. | 514/304 |
| 4,855,422 | 8/1989 | Grimminger et al. | 540/466 |
| 5,654,314 | 8/1997 | Banholzer et al. | 514/291 |

FOREIGN PATENT DOCUMENTS

| | | |
|---|---|---|
| 418716 | 9/1990 | European Pat. Off. . |
| 2168881 | 9/1973 | France . |
| 2208649 | 6/1974 | France . |

OTHER PUBLICATIONS

S. Archer and M.R. Bell, *Chem. Abstr.*, vol. 61, abstract No. 1839f (1964).

E.R. Atkinson et al., "Parasympatholytic (Anticholkinergic) Esters of the Isomeric 2–Tropanols. 1. Glycolates", *J. Med. Chem.* 20(12), pp. 1612–1617 (1977).

L. Larsson et al., "The Hydrogen Bond Condition in Some Anticholinergic Esters of Glycolic Acids. I", *Acta Pharm. Suecica*, pp 304–308 (1974).

Merck Index, 11th ed. Merck & Co. pp. 242 and 802–803 (1989).

K. Nyberg et al., "Investigations of Dithienylglycolic Esters", *Acta Chemica Scandinavica*, 24, pp. 1590–1596 (1970).

*Primary Examiner*—Patricia L. Morris
*Assistant Examiner*—Garth M. Dahlen
*Attorney, Agent, or Firm*—Robert P. Raymond; Alan R. Stempel; Mary-Ellen Devlin

[57] ABSTRACT

The new compounds of formula

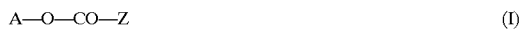

A—O—CO—Z    (I)

(wherein A and Z are defined as explained in the specification) can be prepared by conventional methods; they are suitable as active substances for pharmaceutical compositions.

14 Claims, No Drawings

ESTERS OF BI- AND TRICYCLIC AMINO ALCOHOLS, THEIR PREPARATION AND THEIR USE IN PHARMACEUTICAL COMPOSITIONS

This is a continuation of application Ser. No. 08/117,199, filed Dec. 2, 1993, abandoned.

The invention relates to new esters of bi- and tricyclic amino alcohols, the preparation of these compounds and their use in pharmaceutical compositions.

The new compounds correspond to the formula $$A-O-CO-Z \quad (I)$$

wherein

A represents the group $$\begin{array}{c}(II)\end{array}$$

(structure II: bicyclic amine with $(CH_2)_m$, $(CH_2)_n$ bridges, Q' and Q)

wherein
m represents 0, 1 or 2,
n represents 1 or 2 and m+n<3,
Q represents one of the double-bonded groups
—$CH_2$—$CH_2$—, —$CH_2$—$CH_2$—$CH_2$—,
—CH=CH—, —CH——CH— (with O bridge)

or —$CH_2$—Q"—$(CH_2)_p$— (p=0 or 1)
and
Q' represents the group =NR, the group =NRR' or the group $CH_2$, wherein R represents an optionally halo- or hydroxy-substituted $C_{1-4}$-alkyl group, R' represents a $C_{1-4}$-alkyl group and R and R' together may also form a $C_{4-6}$-alkylene group, and, in the case of quaternary compounds, an equivalent of an anion ($X^\ominus$), is associated with the positive charge of the N-atom, and
Q" has the same meanings as Q', with the exception of $CH_2$, and with the proviso that Q represents —$CH_2$—Q"—$(CH_2)_p$— when Q' represents $CH_2$,
Z represents the group $$\begin{array}{c} R_1 \\ | \\ R_2-C- \\ | \\ R_3 \end{array} \quad (III)$$

wherein
$R_1$ represents H, OH, $CH_2OH$, $C_{1-4}$-alkyl or $C_{1-4}$-alkoxy,
$R_2$ and $R_3$, which may be identical or different and one of which may also be H, represent
  (a) phenyl, furyl, an aromatic group which is isoelectronic with thienyl, $C_{5-7}$-cycloalkyl, pyridyl, $C_{5-7}$-cycloalkenyl or, in particular if m is equal to O and/or Q is equal to —$CH_2$—Q"—$(CH_2)_p$, $R_2$, may also represent thienyl,
  (b) an aliphatic group having up to 20 carbon atoms optionally interrupted by oxygen, or a $C_{1-6}$-alkyl group substituted by phenyl, phenoxy, thienyl, furyl, $C_{5-7}$-cycloalkyl or fluorine,
  (c) the entire group III may also represent the tricyclic group of the formula (IV) or (V) — structures with $R_1$, Y, B, S substituents or a group of formula (VI) — cyclic structure with $(CH_2)_q$ and $R'_1$ wherein B may represent S or CH=CH, $R'_1$ has the same meaning as $R_1$ and may additionally represent phenyl, thienyl, furyl, thiazolyl, thiadiazolyl or methoxyphenyl, Y represents a single bond, an O- or S-atom or one of the groups —$CH_2$—, —$CH_2$—$CH_2$—, —CH=CH—, —$OCH_2$— or —S—$CH_2$— and q represents 1, 2 or 3.

In the compounds of formula I $R_2$ preferably represents OH. The group —OA preferably has an α-configuration and is derived for example from scopine, tropine, granatoline or 6,7-dehydrotropine or the corresponding nor-compounds; —OA may, however, also have the β-configuration as in pseudotropine or pseudoscopine.

Examples of corresponding groups include:

(series of cyclic amine structures with R—N, R—$N^\oplus$—R' $X^\ominus$, HN, $N^\oplus$ $X^\ominus$, and N—R substituents)

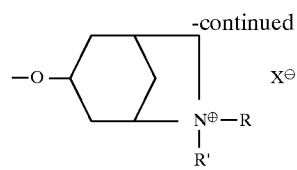

The substituent R is preferably a lower alkyl group, especially $CH_3$, or may also represent, for example, $C_2H_5$, n-$C_3H_7$, i-$C_3H_7$ and R' preferably represents $CH_3$. R and R' together may represent, for example, —$(CH_2)_5$—. The halogen substituent for R is preferably F or, to a lesser extent, Cl. If R represents a halo- or hydroxy-substituted alkyl group it is preferably —$CH_2$—$CH_2F$ or —$CH_2$—$CH_2OH$. Accordingly, the group A represents, for example, the groups of scopine, N-ethylnorscopine, N-isopropylnorscopine, tropine, N-isopropylnortropine, 6,7-dehydrotropine, N-β-fluoroethylnortropine, N-isopropyl-6,7-dehydronortropine, N-methylgranatoline or the corresponding quaternary compounds, the anion preferably being $Br^{\ominus}$ or $CH_3So_3^{\ominus}$.

The group Z may have the following meanings, for example, whilst the aromatic groups may also be substituted, e.g. by $CH_3$, $OCH_3$, F or Cl:

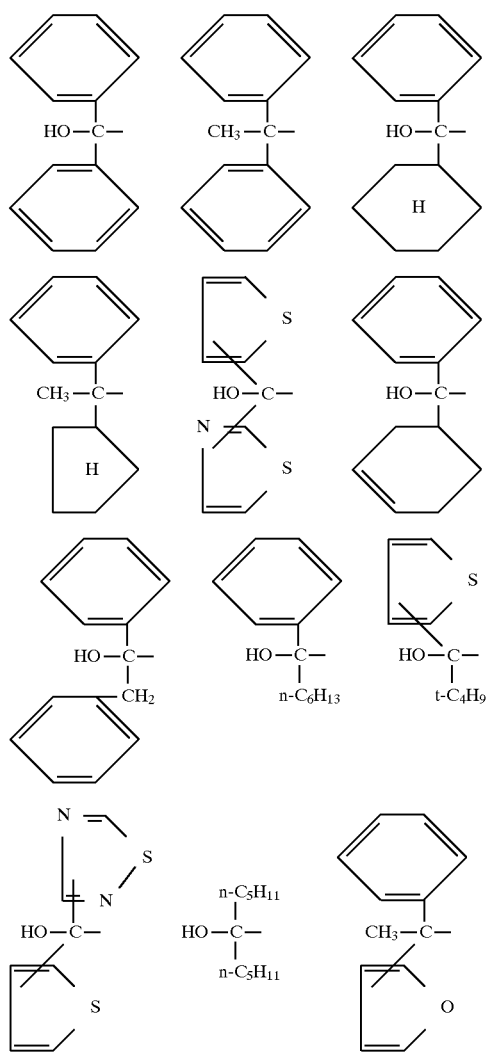

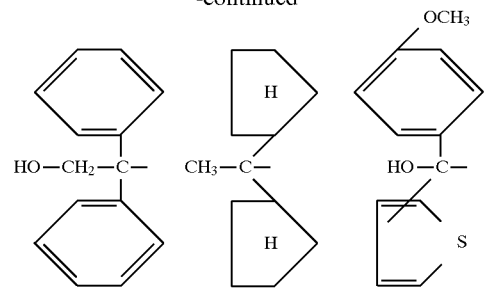

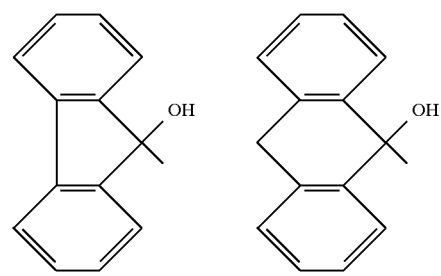

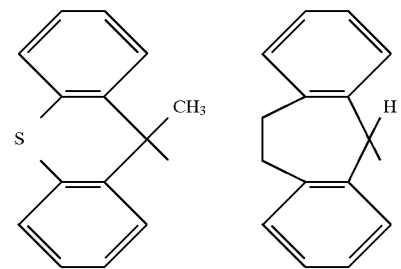

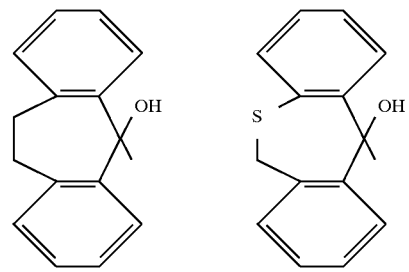

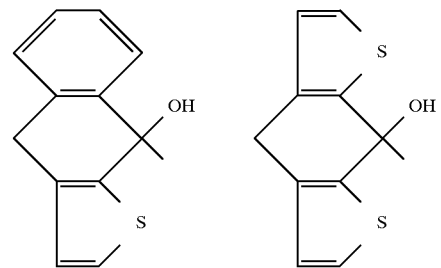

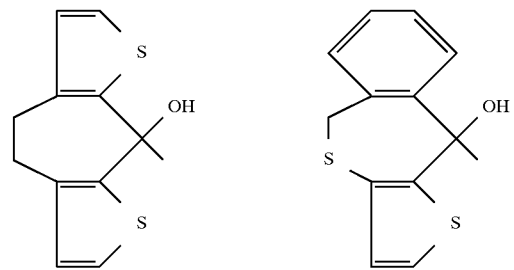

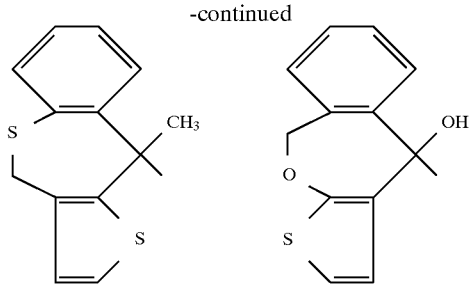

If in the group II m represents O and/or Q represents —CH$_2$—Q"—(CH$_2$)$_p$—, the group III may have the following additional meanings, in particular:

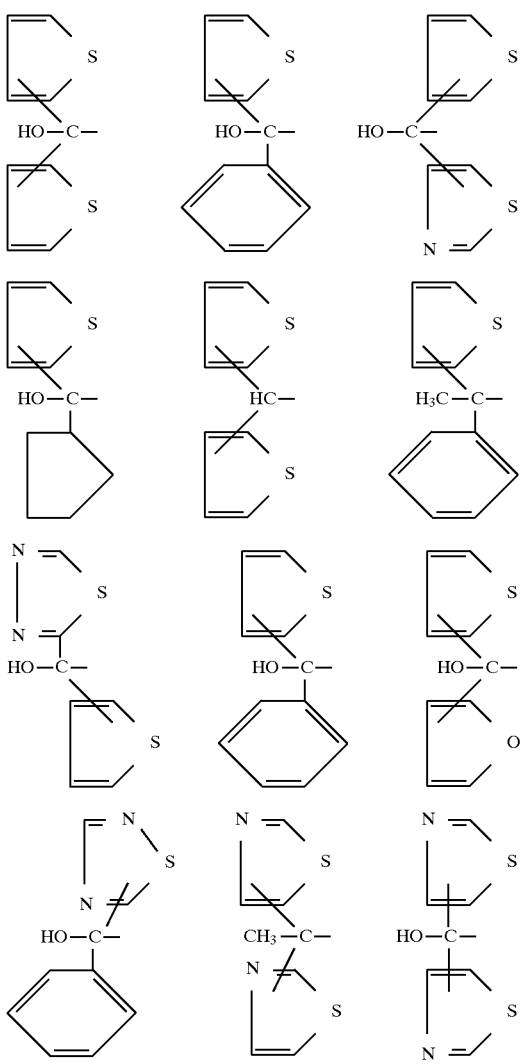

The quaternary compounds of formula I are particularly suitable for therapeutic use, while the tertiary compounds are important not only as active substances but also as intermediate products.

The compounds according to the invention are anticholinergics with a potent and long-lasting effect. At dosages in the microgram range, periods of effect of more than 24 hours are achieved after inhalation. Moreover, the toxicity is in the same range as that of the standard commercial product ipratropium bromide, whilst at the same time the therapeutic effect is in some cases significantly greater.

In accordance with their nature as anticholinergics, the new compounds are suitable, for example, for treating chronically obstructive bronchitis and (slight to moderate) asthma and also for treating vagally induced sinus bradycardia. Whereas in diseases of the respiratory tract it is chiefly recommended to administer the new active substances by inhalation (especially the quaternary compounds), thereby largely eliminating any side effects, the compounds are preferably administered by intravenous or oral route in the case of sinus bradycardia. It has been found to be advantageous that the new compounds have virtually no effect on gastrointestinal motility.

For use, the compounds according to the invention are processed with known excipients and/or carriers to form conventional galenic preparations, e.g. solutions for inhalation, suspensions in liquefied propellant gases, preparations containing liposomes or proliposomes, injectable solutions, plain or coated tablets, capsules, powders for inhalation for use in conventional inhalers.

Examples of formulations (amounts given in percent by weight):

1 Metering aerosol

| Active substance according to the invention | 0.005 |
|---|---|
| Sorbitantrioleate | 0.1 |
| Monofluorotrichloromethane and difluorodichloromethane 2:3 | to 100 |

The suspension is poured into a conventional aerosol container with a metering valve.

Preferably, 50 µl of suspension are dispensed on each actuation. The active substance may also be dispensed in a higher dosage if desired (e.g. 0.02% by weight).

2. Tablets

| Active substance according to the invention | 0.05 |
|---|---|
| Colloidal silica | 0.95 |
| Lactose | 65.00 |
| Potato starch | 28.00 |
| Polyvinylpyrrolidone | 3.00 |
| Na-cellulose glycolate | 2.00 |
| Magnesium stearate | 1.00 |

The ingredients are processed in the usual way to form tablets weighing 200 mg.

The advantageous properties of the new compounds are found for example in their inhibition of broncholysis in rabbits (acetylcholine spasm i.v.). After intravenous administration of the new active substances (dosage 3 µg/kg i.v.) the maximum effect was obtained after 10 to 40 minutes. Even on isolated organs, e.g. on the guinea-pig ileum or rectum, numerous compounds according to the invention were found to have a long duration of activity.

The new compounds may be prepared by methods known per se.

1. Preferably an ester of formula $$Z-CO-OR" \qquad (VII),$$

wherein Z is as hereinbefore defined and R" represents a $C_{1-4}$-alkyl group, preferably methyl or ethyl, is transesterified, in the presence of a conventional transesterification catalyst, with an aminoalcohol of formula

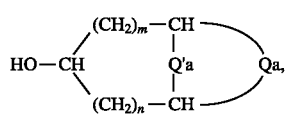

$$\text{HO—CH} \underset{(CH_2)_n—CH}{\overset{(CH_2)_m—CH}{\diagdown}} Q'a \quad Qa, \qquad (VIII)$$

wherein m and n are as hereinbefore defined, $Q'_a$ represents NR' or NH, $Q_a$ has the same meaning as Q, with the proviso that if $Q_a$ represents —$CH_2$—Q"—$(CH_2)_p$—, Q" can only represent NR', and wherein the OH-group is in the α- or β-position, or 2. a reactive derivative (R''' represents a readily cleavable group)

$$Z\text{—CO—OR'''} \qquad (IX)$$

of the acid Z—CO—OH, particularly an acid chloride or imidazolide thereof, is reacted with an alcohol of formula VIII, optionally in excess or in the presence of a tertiary amine such as triethylamine, and optionally the resulting compound a) if $Q'_a$ represents NR', is quaternised with a reactive monoderivative X—R of a corresponding alkane (X=leaving group) or b) if $Q'_a$ represents NH, is quaternised with a terminally disubstituted alkane X—($C_{4-6}$-9alkylene)—X without intermediate isolation or c) if $Q_a$ equals —$CH_2$—NR'—$(CH_2)_p$—, is quaternised with a reactive monoderivative X—R.

Alternatively, starting compounds may be quaternised, in which the starting compound VIII contains R representing a "halo- or hydroxy-substituted alkyl group" instead of R' at the nitrogen atom.

The transesterification according to process 1 is carried out with heating in an organic solvent, e.g. toluene, xylene or heptane, or in a melt, using strong bases such as sodium methoxide, sodium ethoxide, sodium hydride or metallic sodium as catalyst. In order to eliminate the lower alcohol released from the equilibrium, reduced pressure is used, and possibly the alcohol is distilled off azeotropically. The transesterification is carried out at temperatures generally not exceeding 95° C. Frequently, trans-esterification proceeds more easily in a melt. The reaction according to process 2 is carried out in an organic solvent or mixture of solvents which is sufficiently inert under the reaction conditions, e.g. acetone or acetonitrile, at temperatures between about 0° C. and the boiling temperature of the reaction mixture.

The free bases may be obtained from acid addition salts of the tertiary amines, if desired, using suitable basic compounds in a manner known per se. The quaternisation is carried out in suitable solvents, e.g. acetonitrile or acetonitrile/methylene chloride, preferably at ambient temperature; the preferred quaternising reagent is a corresponding alkyl halide, e.g. alkyl bromide, or a corresponding sulphonic acid derivative, e.g. a methane- or toluenesulphonic acid derivative. Transesterification products wherein Q' represents NH are used as starting materials for those compounds in which R and R' together represent a $C_{4-6}$-alkylene group. Conversion into the tertiary and then quaternary compound is carried out using suitable 1,4-, 1,5- or 1,6-dihaloalkanes without intermediate isolation.

The starting compounds, where they have not already been described, may be obtained analogously to known compounds.

EXAMPLES

Methyl di-(2-thienyl)glycolate from dimethyloxalate and 2-thienylmagnesium bromide;

Ethyl di-(2-thienyl)glycolate from (2-thienyl)glyoxylic: acid and 2-thienyllithium;

Ethyl hydroxyphenyl-(2-thienyl)acetate from methylphenylglyoxylate and 2-thienylmagnesium bromide or from methyl (2-thienyl)glyoxylate and phenylmagnesium bromide.

Similarly, methyl 2-thienylglyoxylate and cyclohexyl- or cyclopentylmagnesium bromide may be reacted.

There are also several possible methods of preparing the aminoalcohols.

Pseudoscopine can be obtained according to M. Polonovski et al., Bull. soc. chim. 43, 79 (1928).

Pseudotropenol can be isolated from the mixture (by fractional crystallisation or distillation) which is obtained, for example, according to V. Hayakawa et al., J. Amer.Chem.Soc. 1978, 100(6), 1786 or R. Noyori et al., J.Amer.Chem.Soc. 1974, 96(10), 3336.

N-ethylnorscopine and N-isopropylnorscopine may be prepared by hydrogenolysis from the corresponding N-alkylnorscopolamines analogously to Banholzer DE-A P 3215933. 6-methyl-6-azabicyclo[3.2.1]octan-3-α-ol can be prepared according to F. I. Carroff et al., J. Med.Chem. 30, 805 (1987), and 7-methyl-7-azabicyclo-[2.2.1]heptan-2α-ol may be obtained according to J. R. Pfister et al., J. Pharmac. Sciences 74, 208 (1985).

Starting from 2- or 3-furylglyoxylnitrile the corresponding methylesters may be prepared in conventional manner via the 2- or 3-furylglyoxylic acid obtainable from the starting material. From these methylesters, the corresponding glycolic acid esters may be obtained as described with the organometallic derivatives of 2- or 3-bromothiophene. The organometallic compounds obtainable from 2-, 3- or 4-halopyridine can be reacted with methyl 2- or 3-thienylglyoxylate to obtain the corresponding glycolic acid esters.

Thienylglycolic acid esters in which the thiophene ring in the 2- or 3-position contains fluorine may be obtained, for example, starting from 2-fluorothiophene or 3-fluorothiophene (bromination to obtain 2-bromo-3- fluoro- or 2-bromo-5-fluorothiophene and, after conversion into corresponding organometallic compounds, reaction with suitable glyoxylic acid esters to obtain the glycolic acid esters.

2-fluorothiophene and 3-fluorothiophene may be reacted analogously to Unterhalt, Arch.Pharm. 322, 839 (1989) to obtain the corresponding glyoxylic acid esters which may then in turn be reacted with 2- or 3-thienyl derivatives, for example, to obtain glycolic acid esters, as described above. By a suitable choice of components, symmetrically substituted dithienylglycolic acid esters may be prepared analogously.

A method analogous to benzoin condensation and benzylic acid rearrangement is also possible.

The acid chlorides required may be obtained from the acids and thionyl chloride whilst the imidazolides may be obtained from the acids and carbonyldiimidazole.

The following Examples illustrate the invention without restricting it.

EXAMPLE 1

Benzylic acid scopine ester-methobromide a) Benzylic acid scopine ester from α-chlorodiphenylacetic acid chloride and scopine 26.5 g (0.1 mol) α-chlorodiphenylacetic acid chloride are added to a solution of 31.0 g (0.2 mol) of scopine in 60 ml of anhydrous pyridine at 0° C. within 50 minutes with stirring. After it has all been added the mixture is stirred for 4 hours without cooling and then left to stand for 24 hours. In order to work up the mixture the scopine hydrochloride precipitated is suction filtered. The solution separated off is evaporated down under reduced pressure, the residue is dissolved in a mixture of 600 ml of water and 15 ml of conc. hydrochloric acid and heated to about 80° C. for 10 minutes. At a temperature below 20° C., sodium carbonate is added until a pH of 9 is achieved. The benzylic acid scopine ester is extracted with methylene chloride and the extracts are dried over sodium sulphate. After evaporation and treatment with acetone, white crystals are obtained, m.p. 182°–3° C. (decomp.), yield 31.8 g (87% of theory). Elementary analysis and spectra confirm that the title compound has been obtained which can be converted in the usual way into the hydrochloride, m.p. 256° C. (decomp.; from ethanol).

b) Benzylic acid scopine ester from benzylic acid imidazolide and scopine

A suspension of 7.13 g (0.046 mol) of scopine and 3.2 g (0.0115 mol) of benzylic acid imidazolide in 50 ml of acetone is heated to boiling point. After about 10 minutes a further 9.6 g (0.0345 mol) of benzylic acid imidazolide are gradually added thereto. After the reaction has ended the mixture is cooled with ice/common salt. The crystals precipitated are suction filtered. They may be converted into the hydrochloride, m.p. 256° C. (decomp.; from ethanol). Yield 8.9 g, 53% of theory).

c) Benzylic acid scopine,ester methobromide 7.12 g (0.075 mol) of methylbromide dissolved in acetone are added to a suspension of 5.48 g (0.015 mol) of benzylic acid scopine ester in 120 ml of acetonitrile and 20 ml of carbon tetrachloride and the mixture is left to stand under a slight overpressure until the reaction has ended. The crystals precipitated are suction filtered, washed with cold acetonitrile then with diethylether and after drying (at 40° C. under reduced pressure) recrystallised from methanol/ether, m.p. 200° C. (decomp.). Elementary analysis and spectrum confirm that the desired compound has been obtained.

EXAMPLE 2
1-N-β-Fluoroethylnorscopolamine-methobromide a) 1-N-β-Fluoroethylnorscopolamine-hydrochloride A mixture of 16.3 (0.05 mol) of 1-norscopolamine-hydrochloride, 6.3 g (0.05 mol) of 2-bromofluoroethane, 10.6 g (0.1 mol) of sodium carbonate and 100 ml of acetonitrile is refluxed for 6 hours. Then a further 6.3 g (0.05 mol) of 2-bromofluoroethane and 5.3 g (0.05 mol) of sodium carbonate are added and the mixture is heated for a further 24 hours. Finally, 3.2 g (0.025 mol) of 2-bromofluoroethane and 2.7 g (0.025 mol) of sodium carbonate are added and the mixture is heated for a further 48 hours. It is suction filtered and the solution is concentrated by evaporation. The residue is taken up in methylene chloride, extracted with water and the methylene chloride phase is dried over sodium sulphate. After distillation of the methylene chloride an oily residue is obtained which is reacted in the usual way to form the hydrochloride. From methanol/ether 13.1 g of white crystals are obtained (70.4% of theory), m.p. 197°–8° C. (decomp.).

b) Reaction to form the methobromide 7.0 g (0.021 mol) of the amine liberated in the usual way from the hydrochloride obtained in a) are reacted in 20 ml of absolute acetonitrile with 9.9 g (0.104 mol) of methylbromide for 6 days under a slight overpressure. The crystals precipitated are recrystallised from methanol/ether. 3.9 g of white crystals, m.p. 194° C. (decomp.). Elementary analysis and spectra confirm that the title compound has been obtained.

EXAMPLE 3
Mandelic acid scopine ester methobromide 155.2 g (1.0 mol) of scopine are dissolved in 200 ml of absolute methylene chloride and 116.9 g (0.55 mol) of acetylmandelic acid chloride dissolved in 100 ml of absolute methylene chloride are added dropwise thereto (at 20° C. within 1 hour). (The acetylmandelic acid chloride is obtained from acetylmandelic acid and thionyl chloride). After one hour the scopine hydrochloride precipitated is separated off, the methylene chloride solution is extracted with water and dried.

The combined aqueous phases are made alkaline with sodium carbonate, extracted with methylene chloride and the methylene chloride phase is dried. The solvent is distilled off from the combined methylene chloride solutions. The base which remains is converted into the hydrochloride in the usual way. After recrystallisation from acetonitrile, 124.6 g (67.7% of theory) of white crystals are obtained, m.p. 207° C. (decomp.).

27.5 g (0.075 mol) of the acetyl compound thus obtained are left to stand in 110 ml of 20% hydrochloric acid for 20 hours at ambient temperature. Whilst cooling, the reaction solution is made alkaline and the mandelic acid scopine ester is extracted with methylene chloride. After drying over sodium sulphate and distillation of the solvent, the hydrochloride is prepared in the usual way. From methanol/ether, 22.5 g (92.4% of theory) of white crystals are obtained, m.p. 141°–2° C.

10.7 g (0.037 mol) of the ester liberated from the hydrochloride in the usual way are left to stand for 40 hours in acetonitrile with 17.58 g (0.185 mol) of methylbromide under a slight overpressure.

The crystals precipitated are suction filtered, washed with cold acetonitrile and recrystallised from methanol/ether. 10.0 g (70.4% of theory) of white crystals are obtained, m.p. 223° C. (decomp.).

Elementary analysis and spectra confirm that the title compound has been obtained.

EXAMPLE 4
Xanthene-9-carboxylic acid scopine ester methobromide a) At 20° C., a solution of 11.1 g (0.11 mol) of triethylamine in 20 ml of acetone and 26.9 g (0.11 mol) of xanthene-9-carboxylic acid chloride (obtained from xanthene-9-carboxylic acid and thionyl chloride) in 80 ml of acetone are simultaneously added dropwise to a solution of 15.5 g (0.01 mol) of scopine in 50 ml of acetone at 20° C. After 4 hours a further 1.1 g (0.01 mol) of triethylamine and 2.69 (0.011 mol) of xanthene-9-carboxylic acid chloride are added. After 4 days the mixture is suction filtered and the solvent is distilled off from the solution. Sodium carbonate solution is added to the residue and extracted with methylene chloride. The organic phase is dried over sodium sulphate and the solvent is distilled off. From the residue, the hydrochloride of the resulting xanthene-9- carboxylic acid scopine ester is obtained in the conventional manner; white crystals from acetonitrile/ether, m.p. 223° C. (decomp.); yield 21.8 g.

b) The base is liberated in the usual way from a sufficient quantity of the hydrochloride obtained in a). 36.3 g (0.1 mol) thereof are reacted in a solution of 47.5 g (0.5 mol) of methylbromide in 49 g of acetonitrile for 24 hours under slight overpressure. The crystals obtained are suction filtered, washed with acetone/ether and recrystallised from ethanol. Yield 44.0 g (95.8% of theory), white crystals, m.p. 139° C. The crystals contain 0.5 mol of ethanol. Elementary analysis and spectra confirm the presence of the title compound.

The other compounds according to the invention may also be obtained in accordance with the Examples given above. The compounds melt with decomposition.

TABLE 1

Compounds of formula

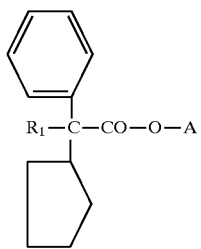

| No. | $R_1$ | A | M.p. [°C.] |
|---|---|---|---|
| 1 | OH | 3α-Tropanyl-methobromide | 275–6 |
| 2 | OH | 3α-Tropanyl-β-fluorethobromide | 205–6 |
| 3 | H | 3α-N-Ethyl-(6β,7β-Epoxy)-nortropanyl-methobromide | 228 |
| 4 | H | 3α-N-Propyl-(6β,7β-Epoxy)-nortropanyl-methobromide | 206–7 |
| 5 | H | 3α-N-Isopropyl-(6β,7β-Epoxy)-nortropanyl-methobromide | 218 |
| 6 | H | 3α-(6β,7β-Epoxy)-tropanyl-methobromide | 207 |
| 7 | H | 3α-(6,7-Dehydro)tropanyl-methobromide | 226–8 |
| 8 | H | 3α-Tropanyl-methobromide | 275–6 |
| 9 | H | 3α-N-Ethyl-nortropanyl-methobromide | 256–7 |
| 10 | H | (−)-3α-N-Isopropylnortropanyl-methobromide | 256 |
| 11 | H | (+)-3α-N-Isopropylnortropanyl-methobromide | 256 |
| 12 | H | 3α-Nortropanyl-8,1'-pyrrolidinium-bromide | 267–70 |
| 13 | H | (+)-3α-Tropanyl-methobromide | 278–81 |
| 14 | H | (−)-3α-Tropanyl-methobromide | 278–81 |

TABLE II

Compounds of formula

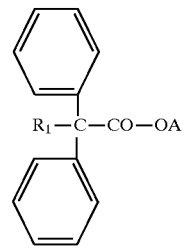

| No. | $R_1$ | A | M.p. [°C.] |
|---|---|---|---|
| 1 | OH | 3α-N-Isopropylnortropanyl-methobromide | 258 |
| 2 | OH | 3α-N-β-Chlorethylnortropanyl-methobromide | 203 |
| 3 | OH | 3α-N-Ethylnortropanyl-methobromide | 269 |
| 4 | OH | 3α-Tropanyl-ethobromide | 258 |
| 5 | OH | 3α-(6β,7β-Epoxy)tropanyl-methobromide | 200 |
| 6 | OH | 3α-N-Ethyl-(6β,7β-Epoxy)-nortropanyl-methobromide | 220–1 |
| 7 | OH | 3α-(6β,7β-Epoxy)-N-isopropyl-nortropanyl-methobromide | 234–5 |
| 8 | OH | 3α-N-Methylgranatanyl-methobromide | 249 |
| 9 | OH | 3α-N-Isopropylgranatanyl-methobromide | 219–20 |
| 10 | OH | 3α-(6,7-Dehydro)tropanyl-methobromide | 207–8 |
| 11 | H | 3α-(6,7-Dehydro)tropanyl-methobromide | 214–5 |
| 12 | OH | 3α-(6,7-Dehydro)-N-isopropyl-nortropanyl-methobromide | 223 |
| 13 | H | 3α-Nortropanyl-8,1'-pyrrolidinium-bromide | 231–2 |

TABLE III

Compounds of formula

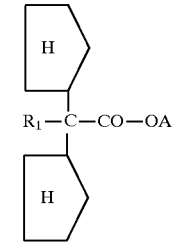

| No. | $R_1$ | A | M.p. [°C.] |
|---|---|---|---|
| 1 | H | 3α-(6β,7β-Epoxy)-tropanyl-methobromide | 213–4 |
| 2 | H | 3α-(6β,7β-Epoxy)-tropanyl-propargochloride | 204–5 |
| 3 | H | 3α-N-Ethyl-(6β,7β-Epoxy)-nortropanyl-methobromide | 201 |
| 4 | H | 3α-(6,7-Dehydro)tropanyl-methobromide | 238–9 |
| 5 | H | 3α-Tropanyl-methobromide | 203–5 |
| 6 | OH | 3α-(6β,7β-Epoxy)tropanyl-metho-methanesulphonate | |

TABLE IV

Compounds of formula

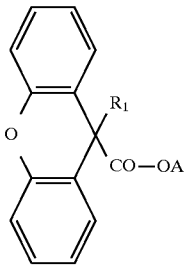

| No. | R₁ | A | M.p. [°C.] |
|---|---|---|---|
| 1 | H | 3α-(6β,7β-Epoxy)-N-n-propyl nortropanyl-methobromide | 213–4 |
| 2 | H | 3α-(6β,7β-Epoxy)-N-isopropyl-nortropanyl-methobromide | 242 |
| 3 | H | 3α-(6β,7β-Epoxy)-N-ethyl-nortropanyl-methobromide | 217 |
| 4 | H | 3α-(6β,7β-Epoxy)tropanyl-methobromide (with crystal ether) | 139 |
| 5 | H | 3α-(6β,7β-Epoxy)tropanyl-ethobromide | 128–31 |
| 6 | H | 3α-Tropanyl-ethobromide | 212–3 |
| 7 | OH | 3α-N-Isopropylnortropanyl-metho-methanesulphonate | 229–32 |
| 8 | H | 3α-N-Isopropylnortropanyl-methobromide | 184–5 |
| 9 | H | 3α-(6,7-Dehydro)-N-isopropyl-nortropanyl-methobromide | 259 |
| 10 | H | 3α-(6,7-Dehydro)-tropanyl-methobromide | 237–8 |

TABLE V

Compounds of formula

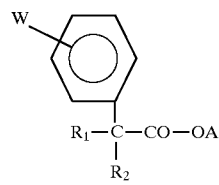

| No. | R₁ | R₂ | W | A | M.p. [°C.] |
|---|---|---|---|---|---|
| 1 | OH | H | H | 3α-(6β,7β-Epoxy)-tropanyl-methobromide | 223 |
| 2 | CH₂OH | H | H | 3α-(6β,7β-Epoxy)-tropanyl-ethobromide | 190 |
| 3 | H | Cyclo-heptyl | H | 3α-(6β,7β-Epoxy)-tropanyl-methobromide | 242 |
| 4 | H | Cyclo-heptyl | H | 3α-(6β,7β-Epoxy)-tropanyl-propobromide | 215–6 |
| 5 | —C₅H₈— | | H | 3α-(6β,7β-Epoxy)-tropanyl-methobromide | 223–4 |
| 6 | CH₂OH | H | H | 3α-(6β,7β-Epoxy)-N-(β-fluorethyl)-nor-tropanyl-methobromide | 194 |
| 7 | CH₂OH | H | H | 3α-(6β,7β-Epoxy)-N-(β-hydroxyethyl)-nortropanyl-methobromide | 211 |
| 8 | OH | C₆H₄ | 4-F | 3α-Tropanyl-methobromide | 220–1 |
| 9 | —C₅H₈— | | H | 3α-Tropanyl-methobromide | 287–9 |
| 10 | —C₅H₈— | | H | 3α-N-Isopropyl-nortropanyl-methobromide | 263 |

TABLE V-continued

Compounds of formula

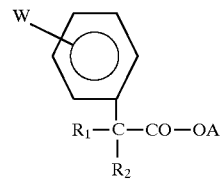

| No. | R₁ | R₂ | W | A | M.p. [°C.] |
|---|---|---|---|---|---|
| 11 | —C₆H₁₀— | | H | 3α-N-Isopropyl-nortropanyl-methobromide | 261 |
| 12 | OH | C₆H₁₁ | H | 3α-(6,7-Dehydro)-tropanyl-methobromide | 233–5 |
| 13 | H | C₆H₁₁ | 3-CH₃ | 3α-N-Isopropyl-nortropanyl-methobromide | 252–4 |
| 14 | H | C₅H₉ | 3-CH₃ | 3α-Nortropanyl-8,1'-pyrrolidinium-bromide | 224–6 |

TABLE VI

Compounds of formula

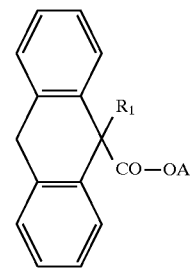

| No. | A | R₁ | M.p. [°C.] |
|---|---|---|---|
| 1 | 3α-(6β,7β-Epoxy)-tropanyl-methobromide.H₂O | H | 176 |
| 2 | 3α-Tropanyl-methobromide | H | |
| 3 | 3α-(6,7-Dehydro)-tropanyl-methobromide | OH | |
| 4 | 3α-(N-β-Fluorethyl)-nortropanyl-methobromide | H | |
| 5 | 3α-Tropanyl-β-fluorethobromide | OH | |
| 6 | 3α-(N-Isopropyl)-granatanyl-methobromide | H | |
| 7 | 3α-(N-Isopropyl)-nortropanyl-methobromide | H | |
| 8 | 3α-(6β,7β-Epoxy)-N-isopropyl-nortropanyl-methobromide | OH | |
| 9 | 3α-(6β,7β-Epoxy)-N-ethylnor-tropanyl-methobromide | OH | |
| 10 | 3α-(N-Ethyl)-nortropanyl-methobromide | OH | |
| 11 | 3α-(N-Methyl)-granatanyl-methobromide | CH₃ | |

TABLE VII

Compounds of formula $$R_1-\underset{\underset{\underset{N}{\overset{\|}{S}}}{\overset{\underset{N}{\overset{\|}{S}}}{|}}}{C}-CO-O-A$$

| No. | A | $R_1$ | M.p. [°C.] |
|---|---|---|---|
| 1 | 3α-(6β,7β-Epoxy)-tropanyl-methobromide | H | |
| 2 | 3α-(6,7-Dehydro)-tropanyl-methobromide | H | |
| 3 | 3α-(6β,7β-Epoxy)-tropanyl-methobromide | Methyl | |
| 4 | 3α-(6,7-Dehydro)-tropanyl-methobromide | Methyl | |
| 5 | 3α-(6β,7β-Epoxy)-tropanyl-methobromide | OH | |
| 6 | 3α-(6,7-Dehydro)-tropanyl-methobromide | OH | |

TABLE VIII

Compounds of formula $$HO-\underset{R_2}{\overset{\underset{N}{\overset{\|}{S}}}{|}}{C}-CO-OA$$

| No. | A | $R_2$ | M.p. [°C.] |
|---|---|---|---|
| 1 | 3α-(6β,7β-Epoxy)-tropanyl-methobromide | Phenyl | |
| 2 | 3α-(6,7-Dehydro)-tropanyl-methobromide | Phenyl | |
| 3 | 3α-(6β,7β-Epoxy)-tropanyl-methobromide | Cyclopentyl | |
| 4 | 3α-(6,7-Dehydro)-tropanyl-methobromide | 3-Thienyl | |
| 5 | 3α-Tropanyl-methobromide | 3-Thienyl | |
| 6 | 3α-(N-Methyl)-granatanyl-methobromide | 3-Thienyl | |

TABLE IX

Compounds of formula $$HO-\underset{R_2}{\overset{\underset{}{\overset{N \hspace{0.3cm} S}{\|}}}{|}}{C}-CO-OA$$

| No. | A | $R_2$ | M.p. [°C.] |
|---|---|---|---|
| 1 | 3α-(6β,7β-Epoxy)-tropanyl-methobromide | Phenyl | |

TABLE IX-continued

Compounds of formula

| No. | A | $R_2$ | M.p. [°C.] |
|---|---|---|---|
| 2 | 3α-(6,7-Dehydro)-tropanyl-methobromide | Phenyl | |
| 3 | 3α-(6β,7β-Epoxy)-tropanyl-methobromide | Cyclopentyl | |
| 4 | 3α-(6,7-Dehydro)-tropanyl-methobromide | 3-Thienyl | |
| 5 | 3α-Tropanyl-methobromide | 3-Thienyl | |
| 6 | 3α-(N-Methyl)-granatanyl-methobromide | 3-Thienyl | |

TABLE X

Compounds of formula $$R_1-\underset{\underset{\underset{N}{\overset{\|}{S}}}{\overset{\underset{N}{\overset{\|}{S}}}{|}}}{C}-CO-OA$$

| No. | A | $R_1$ | M.p. [°C.] |
|---|---|---|---|
| 1 | 3α-(6β,7β-Epoxy)-tropanyl-methobromide | H | |
| 2 | 3α-(6,7-Dehydro)-tropanyl-methobromide | H | |
| 3 | 3α-(6β,7β-Epoxy)-tropanyl-methobromide | Methyl | |
| 4 | 3α-(6,7-Dehydro)-tropanyl-methobromide | Methyl | |
| 5 | 3α-(6β,7β-Epoxy)-tropanyl-methobromide | OH | |
| 6 | 3α-(6,7-Dehydro)-tropanyl-methobromide | OH | |

TABLE XI

Compounds of formula $$HO-\overset{\overset{\bigcirc}{|}}{\underset{\underset{\bigcirc}{|}}{C}}-CO-OA$$

| No. | A | M.p. [°C.] |
|---|---|---|
| 1 | 3α-(6β,7β-Epoxy)-tropanyl | |

TABLE XI-continued

Compounds of formula $$HO-C-CO-OA$$
(with cyclohexyl and cyclopentyl substituents on C)

| No. | A | M.p. [°C.] |
|---|---|---|
| | methobromide | |
| 2 | 3α-(6,7-Dehydro)-tropanyl-methobromide | |
| 3 | 3α-(6β,7β-Epoxy)-tropanyl-ethobromide | |
| 4 | 3α-(6,7-Dehydro)-tropanyl-ethobromide | |
| 5 | 3α-Tropanyl methobromide | |
| 6 | 3α-(N-Methyl)-granatanyl-methobromide | |

TABLE XII

Compounds of formula (structure with S, OH, CO—OA, phenyl groups)

| No. | A | M.p. [°C.] |
|---|---|---|
| 1 | 3α-(6β,7β-Epoxy)-tropanyl-methobromide | |
| 2 | 3α-(6,7-Dehydro)-tropanyl-methobromide | |
| 3 | 3α-(6β,7β-Epoxy)-tropanyl-ethobromide | |
| 4 | 3α-(6,7-Dehydro)-tropanyl-ethobromide | |
| 5 | 3α-Tropanyl methobromide | |
| 6 | 3α-(N-Methyl)-granatanyl-methobromide | |

TABLE XIII

Compounds of formula (structure with S, OH, CO—OA, phenyl groups with CH2 bridge)

| No. | A | M.p. [°C.] |
|---|---|---|
| 1 | 3α-(6β,7β-Epoxy)-tropanyl-methobromide | |
| 2 | 3β-(6,7-Dehydro)-tropanyl-methobromide | |
| 3 | 3α-(6β,7β-Epoxy)-tropanyl-ethobromide | |
| 4 | 3α-(6,7-Dehydro)-tropanyl-ethobromide | |
| 5 | 3α-Tropanyl methobromide | |
| 6 | 3α-(N-Methyl)-granatanyl-methobromide | |

TABLE XIV

Quarternary compounds of formula $$HO-C-CO-OA$$
(with N, S ring and $R_2$ substituent)

| No. | A | $R_2$ | M.p. [°C.] |
|---|---|---|---|
| 1 | 3α-(6β,7β-Epoxy)-tropanyl-methobromide | 2-Thienyl | |
| 2 | 3α-Tropanyl-methobromide | 2-Thienyl | |
| 3 | 3α-(6,7-Dehydro)-tropanyl-methobromide | 2-Thienyl | |
| 4 | 3α-(N-β-Fluorethyl)-nortropanyl-methobromide | 2-Thienyl | |
| 5 | 3α-Tropanyl-β-fluorethobromide | 2-Thienyl | |
| 6 | 3α-(N-Isopropyl)-granatanyl-methobromide | 2-Thienyl | |
| 7 | 3α-(N-Isopropyl)-nortropanyl-methobromide | 2-Thienyl | |
| 8 | 3α-(6β,7β-Epoxy)-N-isopropyl-nortropanyl-methobromide | 2-Thienyl | |
| 9 | 3α-(6β,7β-Epoxy)-N-ethylnor-tropanyl-methobromide | 2-Thienyl | |
| 10 | 3α-(N-Ethyl)-nortropanyl-methobromide | 2-Thienyl | |
| 11 | 3α-(N-Methyl)-granatanyl-methobromide | 2-Thienyl | |
| 12 | 3α-(6β,7β-Epoxy)-N-β-fluoroethyl-nortropanyl-methobromide | 2-Thienyl | |
| 13 | 3α-(6β,7β-Epoxy)-N-n-propyl-nortropanyl-methobromide | 2-Thienyl | |
| 14 | 3α-Tropanyl-β-hydroxyethobromide | 2-Thienyl | |
| 15 | 3α-(6β,7β-Epoxy)-tropanyl-methobromide | Phenyl | |
| 16 | 3α-Tropanyl-methobromide | Phenyl | |
| 17 | 3α-(N-β-Fluoroethyl)- | Phenyl | |

TABLE XIV-continued

Quarternary compounds of formula $$\text{N}-\overset{\text{S}}{\underset{\underset{R_2}{|}}{\text{C}}}-\text{CO}-\text{OA}$$
$$\text{HO}$$

| No. | A | R₂ | M.p. [°C.] |
|---|---|---|---|
|  | nortropanyl-methobromide |  |  |
| 18 | 3α-(6,7-Dehydro)-tropanyl-methobromide | Phenyl |  |
| 19 | 3α-(N-Ethyl)-nortropanyl-methobromide | Phenyl |  |
| 20 | 3α-(N-Isopropyl)-nortropanyl-methobromide | Phenyl |  |
| 21 | 3α-Tropanyl-ethobromide | Phenyl |  |
| 22 | 3α-(N-Ethyl)-nortropanyl-ethobromide | Phenyl |  |
| 23 | 3α-(6β,7β-Epoxy)-tropanyl-ethobromide | Phenyl |  |
| 24 | 3α-Tropanyl-β-fluorthobromide | Phenyl |  |
| 25 | 3α-Tropanyl-methobromide | Cyclohexyl |  |
| 26 | 3α-(N-β-Fluorethyl)-nortropanyl-methobromide | Cyclohexyl |  |
| 27 | 3α-Tropanyl-β-fluorethobromide | Cyclohexyl |  |
| 28 | 3α-Tropanyl-methobromide | Cyclopentyl |  |
| 29 | 3α-Tropanyl-ethobromide | Cyclopentyl |  |
| 30 | 3α-(N-Ethyl)-nortropanyl-methobromide | Cyclopentyl |  |
| 31 | 3α-(N-Isopropyl)-nortropanyl-methobromide | Cyclopentyl |  |
| 32 | 3α-Tropanyl-β-fluorethobromide | Cyclopentyl |  |
| 33 | 3α-(N-β-Fluorethyl)-nortropanyl-methobromide | Cyclopentyl |  |
| 34 | 3α(6,7-Dehydro)-tropanyl-metho-methanesulphonate | 2-Thienyl |  |
| 35 | 3β-(6β,7β-Epoxy)-tropanyl-methobromide | 2-Thienyl |  |
| 36 | 3β-Tropanyl-methobromide | 2-Thienyl |  |
| 37 | 3β-(6,7-Dehydro)-tropanyl-methobromide | 2-Thienyl |  |
| 38 | 3α(6,7-Dehydro)-tropanyl-methobromide | 3-Thienyl |  |
| 39 | 3α-(6β,7β-Epoxy)-tropanyl-methobromide | 3-Thienyl |  |
| 40 | (+)-Enantiomer of No. 1 |  |  |
| 41 | (−)-Enantiomer of No. 1 |  |  |
| 42 | 3α-(6β,7β-Epoxy)tropanyl-methobromide | 2-Furyl |  |
| 43 | 3α-(6,7-Dehydro)-tropanyl-methobromide | 2-Furyl |  |
| 44 | 3α-Tropanyl-methobromide | 2-Furyl |  |
| 45 | 3α-(6β,7β-Epoxy)-tropanyl methobromide | 2-Pyridyl |  |
| 46 | 3α-(6,7-Dehydro)-tropanyl methobromide | 2-Pyridyl |  |
| 47 | 3α-Tropanyl-methobromide | 2-Pyridyl |  |
| 48 | 3α-Tropanyl-methobromide | 3-Thienyl |  |
| 49 | 3α-(6,7-Dehydro)-tropanyl methobromide | Cyclopentyl |  |
| 50 | 3α-(6β,7β-Epoxy)-tropanyl methobromide | Cyclohexyl |  |
| 51 | 3α-(6,7-Dehydro)-tropanyl methobromide | Cyclohexyl |  |
| 52 | 3α-(6β,7β-Epoxy)-tropanyl methobromide | Cyclopentyl |  |

TABLE XV

Compounds of formula $$R_a-\overset{\text{S}}{\underset{\underset{R_2}{|}}{\text{C}}}-\text{CO}-\text{OA}$$
$$\text{HOCH}_2$$

| No. | A | R₂ | Rₐ | M.p [°C.] |
|---|---|---|---|---|
| 1 | 3α-(6β,7β-Epoxy)-tropanyl-methobromide | 2-Thienyl | 5-Methyl |  |
| 2 | 3α-(6,7-Dehydro)-tropanyl-methobromide | 2-Thienyl | 5-Methyl |  |
| 3 | 3α-Tropanyl-methobromide | 2-Thienyl | 5-Methyl |  |
| 4 | 3α-(6β,7β-Epoxy)-tropanyl-methobromide | 2-(5-Methyl)-thienyl | 5-Methyl |  |
| 5 | 3α-(6,7-Dehydro)-tropanyl-methobromide | 2-(5-Methyl)-thienyl | 5-Methyl |  |
| 6 | 3α-Tropanyl-methobromide | 2-(5-Methyl)-thienyl | 5-Methyl |  |
| 7 | 3α-(6β,7β-Epoxy)-tropanyl-methobromide | 2-Thienyl | 5-Fluoro |  |
| 8 | 3α-(6,7-Dehydro)-tropanyl-methobromide | 2-Thienyl | 5-Fluoro |  |
| 9 | 3α-Tropanyl-methobromide | 2-Thienyl | 5-Fluoro |  |
| 10 | 3α-(6β,7β-Epoxy)-tropanyl-methobromide | 2-(5-Fluoro)-thienyl | 5-Fluoro |  |
| 11 | 3α-(6,7-Dehydro)-tropanyl-methobromide | 2-(5-Fluoro)-thienyl | 5-Fluoro |  |
| 12 | 3α-Tropanyl-methobromide | 2-(5-Fluoro)-thienyl | 5-Fluoro |  |

TABLE XVI

Compounds of formula $$\overset{\text{N}}{\underset{\underset{R_2}{|}}{\text{C}}}\diagdown\overset{\text{S}}{\diagup}$$
$$\text{HO}-\text{C}-\text{CO}-\text{OA}$$

| No. | A | R₂ | M.p. [°C.] |
|---|---|---|---|
| 1 | 3α-(6β,7β-Epoxy)-tropanyl methobromide | Phenyl |  |
| 2 | 3α-(6,7-Dehydro)-tropanyl methobromide | Phenyl |  |
| 3 | 3α-(6β,7β-Epoxy)-tropanyl methobromide | 3-Thienyl |  |
| 4 | 3α-(6,7-Dehydro)-tropanyl methobromide | 3-Thienyl |  |
| 5 | 3α-Tropanyl methobromide | 3-Thienyl |  |
| 6 | 3α-(N-Methyl)-granatanyl methobromide | 3-Thienyl |  |

TABLE XVII

Compounds of formula

[structure: dibenzosuberyl carbinol with OH and CO—OA]

| No. | A | M.p.[°C.] |
|---|---|---|
| 1 | 3α-(6β,7β-Epoxy)-tropanyl-methobromide | |
| 2 | 3α-Tropanyl-methobromide | |
| 3 | 3α-(6,7-Dehydro)-tropanyl-methobromide | |
| 4 | 3α-(N-β-Fluorethyl)-nortropanyl-methobromide | |
| 5 | 3α-Tropanyl-β-fluorethobromide | |
| 6 | 3α-(N-Isopropyl)-granatanyl-methobromide | |
| 7 | 3α-(N-Isopropyl)-nortropanyl-methobromide | |
| 8 | 3α-(6β,7β-Epoxy)-N-isopropyl-nortropanyl-methobromide | |
| 9 | 3α-(6β,7β-Epoxy)-N-ethylnor-tropanyl-methobromide | |
| 10 | 3α-(N-Ethyl)-nortropanyl-methobromide | |
| 11 | 3α-(N-Methyl)-granatanyl-methobromide | |
| 12 | 3α-(6β,7β-Epoxy)-N-β-fluoroethyl-nortropanyl-methobromide | |
| 13 | 3α-(6β,7β-Epoxy)-N-n-propyl-nortropanyl-methobromide | |
| 14 | 3α-Tropanyl-β-hydroxyethobromide | |
| 15 | 3α(6,7-Dehydro)-tropanyl-metho-methanesulphonate | |
| 16 | 3β-(6β,7β-Epoxy)-tropanyl-methobromide | |
| 17 | 3β-Tropanyl-methobromide | |
| 18 | 3β-(6,7-Dehydro)-tropanyl-methobromide | |

TABLE XVIII

Compounds of formula

[structure with S, R1, CO—OA]

| No. | A | R1 | M.p. [°C.] |
|---|---|---|---|
| 1 | 3α-(6β,7β-Epoxy)-tropanyl methobromide | OH | |
| 2 | 3α-(6,7-Dehydro)-tropanyl methobromide | OH | |
| 3 | 3α-(6β,7β-Epoxy)-tropanyl methobromide | Methyl | |
| 4 | 3α-(6,7-Dehydro)-tropanyl methobromide | Methyl | |
| 5 | 3α-Tropanyl methobromide | H | |
| 6 | 3α-(N-Ethyl)-nortropanyl methobromide | H | |

TABLE A

Compounds of formula

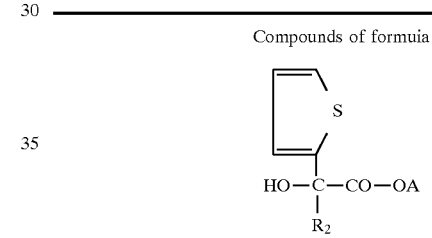

| No. | A | R2 | Base Mp. [°C.] | Hydro-chloride |
|---|---|---|---|---|
| 1 | 3α-(6β,7β-Epoxy)-tropanyl | 2-Thienyl | 149–50 | 238–41 |
| 2 | 3α-Tropanyl | 2-Thienyl | 167–8 | 253 |
| 3 | 3α-(6,7-Dehydro)-tropanyl | 2-Thienyl | 164–5 | |
| 4 | 3α-(N-β-Fluorethyl)-nortropanyl | 2-Thienyl | | 236 |
| 5 | 3α-(N-Isopropyl)-granatanyl | 2-Thienyl | | 232 |
| 6 | 3α-(N-Isopropyl)-nortropanyl | 2-Thienyl | | 250 |
| 7 | 3α-(6β,7β-Epoxy)-N-iso-propylnortropanyl | 2-Thienyl | | 206 |
| 8 | 3α-(6β,7β-Epoxy)-N-ethyl-nortropanyl | 2-Thienyl | | 212–3 |
| 9 | 3α-(N-Ethyl)-nortropanyl | 2-Thienyl | | 256–7 |
| 10 | 3α-(N-Methyl)-granatanyl | 2-Thienyl | | 241 |
| 11 | 3α-(6β,7β-Epoxy)-N-β-fluorethylnortropanyl | 2-Thienyl | | 188–90 |
| 12 | 3α-(6β,7β-Epoxy)-N-n-propylnortropanyl | 2-Thienyl | 104–6 | |
| 13 | 3α(6β,7β-Epoxy)-N-n-butylnortropanyl | 2-Thienyl | | 225–7 |
| 14 | 3α-(6β,7β-Epoxy)-tropanyl | Phenyl | | 246–7 |
| 15 | 3α-Tropanyl | Phenyl | | 243–4 |
| 16 | 3α-(N-β-Fluoroethyl)-nortropanyl | Phenyl | | 219–20 |
| 17 | 3α-(6,7-Dehydro)-tropanyl | Phenyl | 181–3 | |
| 18 | 3α-(N-Ethyl)-nortropanyl | Phenyl | | 231–2 |
| 19 | 3α-(N-Isopropyl)-nortropanyl | Phenyl | | 246–7 |
| 20 | 3α-Tropanyl | Cyclohexyl | | 260 |

TABLE A-continued

Compounds of formula

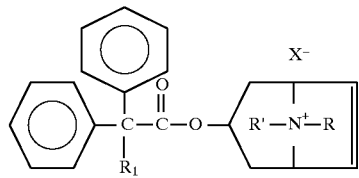

| No. | A | $R_2$ | Base | Mp. [°C.] Hydrochloride |
|---|---|---|---|---|
| 21 | 3α-(N-β-Fluoroethyl)-nortropanyl | Cyclohexyl | | 203–4 |
| 22 | 3α-(6β,7β-Epoxy)-tropanyl | Cyclopentyl | | 237 |
| 23 | 3α-Tropanyl | Cyclopentyl | | 260 |
| 24 | 3α-(N-β-Fluoroethyl)-nortropanyl | Cyclopentyl | | 182–3 |
| 25 | 3α-(N-Ethyl)-nortropanyl | Cyclopentyl | | 227–8 |
| 26 | 3α-(N-Isopropyl)-nortropanyl | Cyclopentyl | | 174–5 |
| 27 | 3β-(6β,7β-Epoxy)-tropanyl | 2-Thienyl | | 240–2 |
| 28 | 3β-Tropanyl | 2-Thienyl | | 217–9 |
| 29 | 3β-(6,7-Dehydro)-tropanyl | 2-Thienyl | | 233–5 |
| 30 | 3α-(6,7-Dehydro)-tropanyl | 3-Thienyl | | 247–8 |
| 31 | 3α-(6β,7β-Epoxy)-tropanyl | 3-Thienyl | | 242–3 |
| 32 | 3α-(6β,7β-Epoxy)-tropanyl | 2-Furyl | | |
| 33 | 3α-(6,7-Dehydro)-tropanyl | 2-Furyl | | |
| 34 | 3α-Tropanyl | 2-Furyl | | |
| 35 | 3α-Tropanyl | 2-Pyridyl | | |
| 36 | 3α-(6β,7β-Epoxy)-tropanyl | 2-Pyridyl | | |
| 37 | 3α-(6,7-Dehydro)-tropanyl | 2-Pyridyl | | |
| 38 | 3α-Tropanyl | 3-Thienyl | | |
| 39 | 3α-(6,7-Dehydro)-tropanyl | Cyclopentyl | | |
| 40 | 3α-(6β,7β-Epoxy)-tropanyl | Cyclohexyl | | |
| 41 | 3α-(6,7-Dehydro)-tropanyl | Cyclohexyl | | |

Note: all hydrochlorides melt with decomposition.

We claim:

1. A compound of formula wherein

R is an optionally halo- or hydroxy-substituted $C_{1-4}$-alkyl group;

R' is a $C_{1-4}$-alkyl group; or

R and R' together form a $C_{4-6}$-alkylene group;

$X^-$ is an anion;

and $R_1$ is H, OH, $CH_2OH$, $C_{1-4}$-alkyl or $C_{1-4}$-alkoxy.

2. The compound according to claim 1, wherein $X^-$ is bromide.

3. The compound according to claim 1, wherein $R_1$ is OH, $CH_3$ or $CH_2OH$.

4. The compound according to claim 1, wherein R is methyl and R' is methyl, ethyl, n-propyl or i-propyl.

5. A pharmaceutical composition comprising a compound according to any one of claims 1–4 and a pharmaceutically acceptable excipient or carrier.

6. A method for treating a disease which is responsive to an anti-cholinergic agent in a warm-blooded animal, comprising the step of administering to said animal a therapeutically effective amount of the pharmaceutical composition according to claim 5.

7. The method according to claims 6, wherein said pharmaceutical composition is administered by inhalation.

8. The method according to claim 6, wherein said pharmaceutical composition is administered intravenously or orally.

9. A method for treating a respiratory tract disease in a warm-blooded animal, comprising the step of administering to said animal a therapeutically effective amount of the pharmaceutical composition according to claim 5.

10. The method according to claim 9, wherein said pharmaceutical composition is administered by inhalation.

11. The method according to claim 9, wherein said pharmaceutical composition is administered Intravenously or orally.

12. A method for treating sinus bradycardia in a warm-blooded animal, comprising the step of administering to said animal a therapeutically effective amount of the pharmaceutical composition according to claim 5.

13. The method according to claim 12, wherein said pharmaceutical composition is administered by inhalation.

14. The method according to claim 12, wherein said pharmaceutical composition is administered intravenously or orally.

* * * * *